US00RE37704E

(19) United States
(12) Reissued Patent
Eshel

(10) Patent Number: US RE37,704 E
(45) **Date of Reissued Patent: *May 14, 2002**

(54) THERMAL TREATMENT APPARATUS

(75) Inventor: Uzi Eshel, Herzlia Pituach (IL)

(73) Assignee: ArgoMed Ltd., Herzlia (IL)

( * ) Notice: This patent is subject to a terminal disclaimer.

(21) Appl. No.: 09/534,842

(22) Filed: Mar. 28, 2000

Related U.S. Patent Documents

Reissue of:
(64) Patent No.: 5,549,559
Issued: Aug. 27, 1996
Appl. No.: 08/212,197
Filed: Mar. 11, 1994

(30) Foreign Application Priority Data

Mar. 22, 1990 (IL) ..... 93842

(51) Int. Cl.[7] ..... A61F 7/12
(52) U.S. Cl. ..... 604/113; 604/97.01; 604/153; 606/28
(58) Field of Search ..... 604/27, 28, 48, 604/97.01, 101.01, 113, 114, 151–153; 606/27, 28, 194; 607/105, 126

(56) References Cited

U.S. PATENT DOCUMENTS

| | | | |
|---|---|---|---|
| 612,724 | A | 10/1898 | Hamilton |
| 827,099 | A | 7/1906 | Hofmann |
| 899,477 | A | 9/1908 | Williams |
| 1,011,606 | A | 12/1911 | Fulton |
| 1,393,153 | A | 10/1921 | Morris |

(List continued on next page.)

FOREIGN PATENT DOCUMENTS

| | | | |
|---|---|---|---|
| DE | 895046 | | 7/1953 |
| EP | 0105677 | | 9/1983 |
| EP | 0341988 | | 11/1989 |
| EP | 0449472 | A | 2/1991 |
| EP | 0543309 | A1 | 5/1993 |
| EP | 0672401 | A3 | 9/1995 |
| EP | 0672401 | A2 | 9/1995 |
| EP | 0733379 | A1 | 9/1996 |
| EP | 0753289 | A1 | 1/1997 |
| EP | 0790041 | A2 | 8/1997 |

(List continued on next page.)

OTHER PUBLICATIONS

Abstract, Kaver et al., "A New Transurethral Water–Induced Thermal (WIR) Dilation Device for the Treatment of BPH," presented at SIU, Sydney, Australia, Poster Session 26, BPH, Thermotherapy and Hypothermia (Sep. 1994).

European Search Report, Application No. EP 95 10 3189 dated Sep. 26, 1995.

European Search Report, Application No. EP 97 10 6282 dated Dec. 7, 1999.

*Primary Examiner*—Anhtuan T. Nguyen
(74) *Attorney, Agent, or Firm*—Myers Bigel Sibley & Sajovec, P.A.

(57) ABSTRACT

Thermal treatment apparatus for thermally treating selected tissues of a subject located in or near a body cavity, includes a catheter insertable into the subject's body cavity and having a proximal end formed with an inflatable anchoring section for anchoring the catheter in the body cavity, a distal end to be located externally of the body cavity, and an inflatable heating section adjacent the proximal end to be located near the tissue to be heated. The catheter is formed with passageways extending from the distal end to the inflatable heating section for circulating heated fluid through the inflatable heating section but not through the inflatable anchoring section, and a further passageway from the distal end to the inflatable anchoring section for inflating the inflatable anchoring section with a non-heated fluid. The inflatable heating section and the tissue in its proximity may thus be heated to a desired high temperature without correspondingly heating the inflatable anchoring section and the tissue in its proximity.

32 Claims, 5 Drawing Sheets

U.S. PATENT DOCUMENTS

| | | | |
|---|---|---|---|
| 1,584,464 | A | 5/1926 | Maranville |
| 1,620,929 | A | 3/1927 | Wallerich |
| 1,652,954 | A | 12/1927 | Pierce |
| 1,690,995 | A | 11/1928 | Pratt |
| 1,764,838 | A | 6/1930 | Horne |
| 1,786,373 | A | 12/1930 | Walker |
| 1,827,306 | A | 10/1931 | Chapman et al. |
| 1,904,020 | A | 4/1933 | Wappler |
| 2,024,301 | A | 12/1935 | Norwood |
| 2,043,083 | A | 6/1936 | Wappler |
| 2,026,747 | A | 10/1936 | Nemzek |
| 2,058,780 | A | 10/1936 | Elliott |
| 2,074,634 | A | 3/1937 | Ackermann |
| 2,076,638 | A | 4/1937 | Haynos |
| 2,077,453 | A | 4/1937 | Albright |
| 2,078,786 | A | 4/1937 | Wood |
| 2,103,371 | A | 12/1937 | Kleckner |
| 2,168,427 | A | 8/1939 | McConkey |
| 2,190,383 | A | 2/1940 | Newman |
| 2,190,384 | A | 2/1940 | Newman |
| 2,192,768 | A | 3/1940 | Cross |
| 2,466,042 | A | 4/1949 | Reich |
| 2,734,508 | A | 2/1956 | Kozinski |
| 2,777,442 | A | 1/1957 | Zelano |
| 2,777,445 | A | 1/1957 | Hart |
| 2,849,001 | A | 8/1958 | Oddo |
| 3,154,077 | A | 10/1964 | Cannon |
| 3,227,154 | A | 1/1966 | Cook |
| 3,369,549 | A | 2/1968 | Armao |
| 3,417,746 | A | 12/1968 | Moore et al. |
| 3,625,793 | A | 12/1971 | Sheridan et al. |
| 3,645,265 | A | 2/1972 | Majzlin |
| 3,811,450 | A | 5/1974 | Lord |
| 3,848,602 | A | 11/1974 | Gutnick |
| 3,848,607 | A | 11/1974 | St. Clair |
| 4,091,672 | A | 5/1978 | Amrine et al. |
| 4,112,943 | A | 9/1978 | Adams |
| 4,137,922 | A | 2/1979 | Leininger et al. |
| 4,143,649 | A | 3/1979 | Foti |
| 4,160,455 | A | 7/1979 | Law |
| 4,185,948 | A | 1/1980 | Maguire |
| 4,244,377 | A | 1/1981 | Grams |
| 4,335,726 | A | 6/1982 | Kolstedt |
| 4,367,747 | A | 1/1983 | Witzel |
| 4,469,103 | A | 9/1984 | Barrett |
| 4,530,647 | A | 7/1985 | Uno |
| 4,552,557 | A | 11/1985 | Rangaswamy |
| 4,574,752 | A | 3/1986 | Reichert, Jr. et al. |
| 4,610,660 | A | 9/1986 | Rosenberg |
| 4,628,931 | A | 12/1986 | Barrett |
| 4,636,195 | A | 1/1987 | Wolinsky |
| 4,655,746 | A | 4/1987 | Daniels |
| 4,662,368 | A | 5/1987 | Hussein et al. |
| 4,671,795 | A | 6/1987 | Mulchin |
| 4,672,962 | A | 6/1987 | Hershenson |
| 4,676,258 | A | 6/1987 | Inokuchi et al. |
| 4,686,965 | A | 8/1987 | Bonnet et al. |
| 4,686,985 | A | 8/1987 | Lottick |
| 4,709,698 | A | 12/1987 | Johnston et al. |
| 4,710,169 | A | 12/1987 | Christopher |
| 4,754,752 | A | 7/1988 | Ginsburg et al. |
| 4,787,388 | A | 11/1988 | Hofmann |
| 4,793,351 | A | 12/1988 | Landman et al. |
| 4,793,352 | A | 12/1988 | Eichenlaub |
| 4,799,479 | A | 1/1989 | Spears |
| 4,819,751 | A | 4/1989 | Shimada et al. |
| 4,823,812 | A | 4/1989 | Eshel et al. |
| 4,824,436 | A | 4/1989 | Wolinksy |
| 4,832,691 | A | 5/1989 | Witzel |
| 4,860,744 | A | 8/1989 | Johnson et al. |
| 4,865,047 | A | 9/1989 | Chou et al. |
| 4,893,623 | A | 1/1990 | Rosenbluth |
| 4,932,938 | A | 6/1990 | Goldberg et al. |
| 4,932,956 | A | 6/1990 | Reddy et al. |
| 4,946,449 | A | 8/1990 | Davis, Jr. |
| 4,949,718 | A | 8/1990 | Neuwirth et al. |
| 4,950,227 | A | 8/1990 | Savin et al. |
| 4,955,859 | A | 9/1990 | Zilber |
| 4,967,765 | A | 11/1990 | Turner et al. |
| 4,973,301 | A | 11/1990 | Nissenkorn |
| 4,995,872 | A | 2/1991 | Ferrara |
| 5,007,437 | A | 4/1991 | Sterzer |
| 5,019,075 | A | 5/1991 | Spears et al. |
| 5,035,694 | A | 7/1991 | Kasprzyk et al. |
| 5,041,092 | A | 8/1991 | Barwick |
| 5,045,056 | A | 9/1991 | Behl |
| 5,059,169 | A | 10/1991 | Zilber |
| 5,061,241 | A | 10/1991 | Stephens, Jr. et al. |
| 5,084,044 | A | 1/1992 | Quint |
| 5,098,374 | A | 3/1992 | Othel-Jacobsen et al. |
| 5,105,808 | A | 4/1992 | Neuwirth et al. |
| 5,112,306 | A | 5/1992 | Burton et al. |
| 5,151,100 | A | 9/1992 | Abele et al. ..... 600/28 |
| 5,159,925 | A | 11/1992 | Neuwirth et al. |
| 5,176,626 | A | 1/1993 | Soehendra |
| 5,188,596 | A | 2/1993 | Condon et al. |
| 5,195,565 | A | 3/1993 | Owen et al. |
| 5,195,965 | A | 3/1993 | Shautha ..... 604/114 X |
| 5,220,927 | A | 6/1993 | Astrahan et al. |
| 5,234,004 | A | 8/1993 | Hascoet et al. |
| 5,257,977 | A | 11/1993 | Eshel ..... 604/113 |
| 5,269,758 | A | 12/1993 | Taheri ..... 604/96.01 |
| 5,269,802 | A | 12/1993 | Garber |
| 5,281,213 | A | 1/1994 | Milder et al. |
| 5,286,259 | A | 2/1994 | Ganguly et al. |
| 5,306,241 | A | 4/1994 | Samples |
| 5,312,343 | A | 5/1994 | Krog et al. |
| 5,314,443 | A | 5/1994 | Rudnick |
| 5,322,501 | A | 6/1994 | Mahmud-Durrani |
| 5,328,471 | A | 7/1994 | Slepian |
| 5,372,600 | A | 12/1994 | Beyar et al. |
| 5,385,540 | A | 1/1995 | Abbott et al. |
| 5,391,196 | A | 2/1995 | Devonec |
| 5,403,281 | A | 4/1995 | O'Neill et al. |
| 5,419,763 | A | 5/1995 | Hildebrand |
| 5,431,648 | A | 7/1995 | Lev |
| 5,439,446 | A | 8/1995 | Barry |
| 5,451,218 | A | 9/1995 | Moore |
| 5,478,349 | A | 12/1995 | Nicholas |
| 5,480,417 | A | 1/1996 | Hascoet et al. |
| 5,496,271 | A | 3/1996 | Burton et al. |
| 5,496,311 | A | 3/1996 | Abele et al. |
| 5,499,994 | A | 3/1996 | Tihon et al. |
| 5,509,929 | A | 4/1996 | Hascoet et al. |
| 5,514,092 | A | 5/1996 | Forman et al. |
| 5,514,095 | A | 5/1996 | Brightbill et al. |
| 5,514,178 | A | 5/1996 | Torchio |
| 5,518,498 | A | 5/1996 | Lindenberg et al. |
| 5,571,153 | A | 11/1996 | Wallsten |
| 5,578,008 | A | 11/1996 | Hara |
| 5,588,965 | A | 12/1996 | Burton et al. |
| 5,609,583 | A | 3/1997 | Hakki et al. |
| 5,624,392 | A | 4/1997 | Saab ..... 604/113 X |
| 5,685,847 | A | 11/1997 | Barry ..... 604/96.01 |
| 5,718,686 | A | 2/1998 | Davis ..... 604/101.05 |
| 5,766,209 | A | 6/1998 | Devonec ..... 604/8 |
| 5,785,641 | A | 7/1998 | Davis ..... 604/101.05 X |
| 5,843,144 | A | 12/1998 | Rudie et al. ..... 607/101 |
| 5,876,517 | A | 3/1999 | Jeannier ..... 148/264 |
| 5,916,195 | A | 6/1999 | Eshel et al. ..... 604/96.01 |

FOREIGN PATENT DOCUMENTS

| | | | |
|---|---|---|---|
| EP | 0801938 | A2 | 10/1997 |
| EP | 0801938 | A3 | 8/1999 |
| FR | 439636 | | 6/1912 |
| FR | 774318 | | 12/1951 |
| FR | 100300 | | 2/1952 |
| FR | 1328484 | | 2/1978 |
| FR | 1550927 | | 3/1980 |
| GB | 287772 | | 3/1928 |
| GB | 315971 | | 7/1929 |
| GB | 317604 | | 8/1929 |
| GB | 658662 | | 10/1951 |
| GB | 151004 | | 2/1976 |
| GB | 1563795 | | 4/1980 |
| GB | 20696063 | | 8/1981 |
| JP | 52-104397 | | 1/1977 |
| JP | S56-16437 | | 3/1979 |
| JP | 61-89330 | | 4/1983 |
| JP | 60235940 | A | 9/1984 |
| JP | 62005045 | A | 1/1985 |
| JP | 63-43661 | | 2/1988 |
| JP | 63-222759 | | 9/1988 |
| JP | 1-263440 | | 10/1989 |
| WO | WO91/12846 | | 9/1991 |
| WO | WO92/00710 | | 1/1992 |
| WO | WO92/04934 | | 4/1992 |
| WO | WO92/07622 | | 5/1992 |
| WO | WO92/18199 | | 10/1992 |
| WO | WO93/04727 | | 3/1993 |
| WO | 94/10948 | | 5/1994 |
| WO | PCT/FR95/00869 | | 6/1995 |
| WO | WO98/00192 | | 1/1998 |

FIG.1
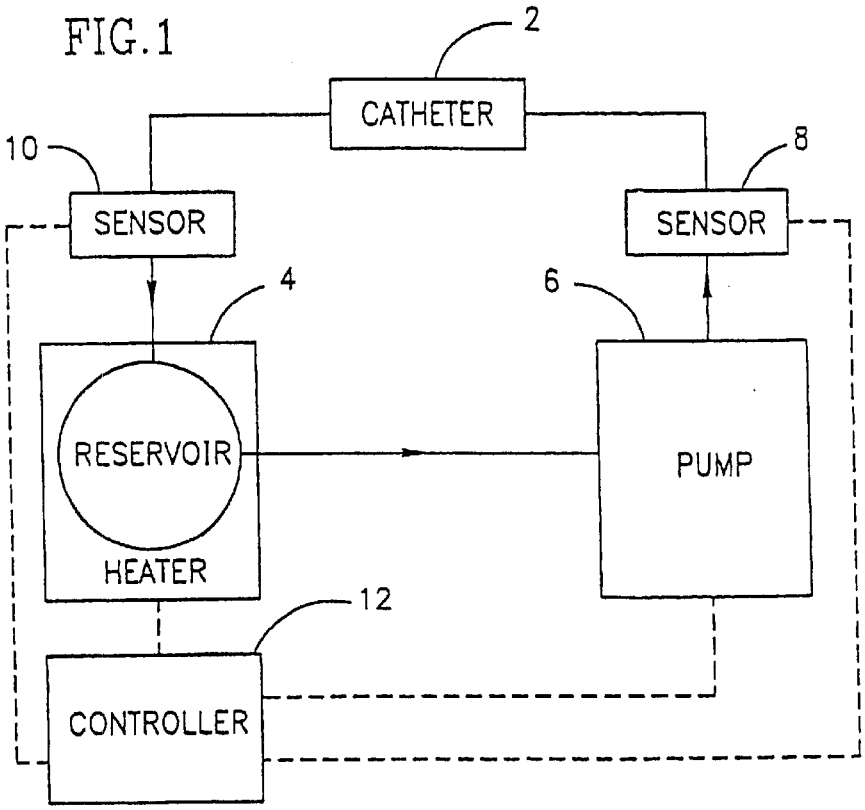
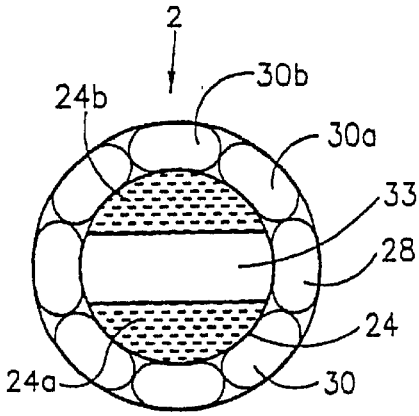
FIG.4
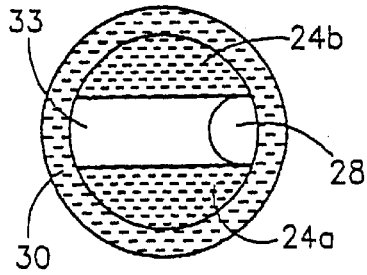
FIG.5
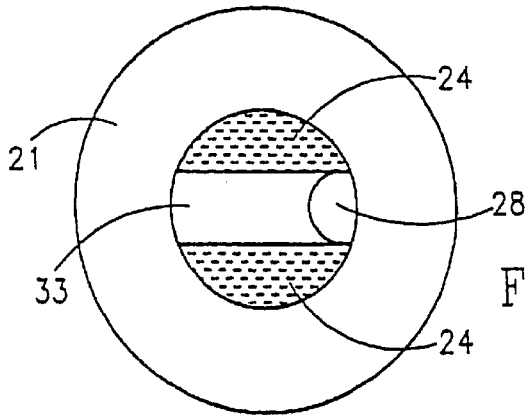
FIG.6

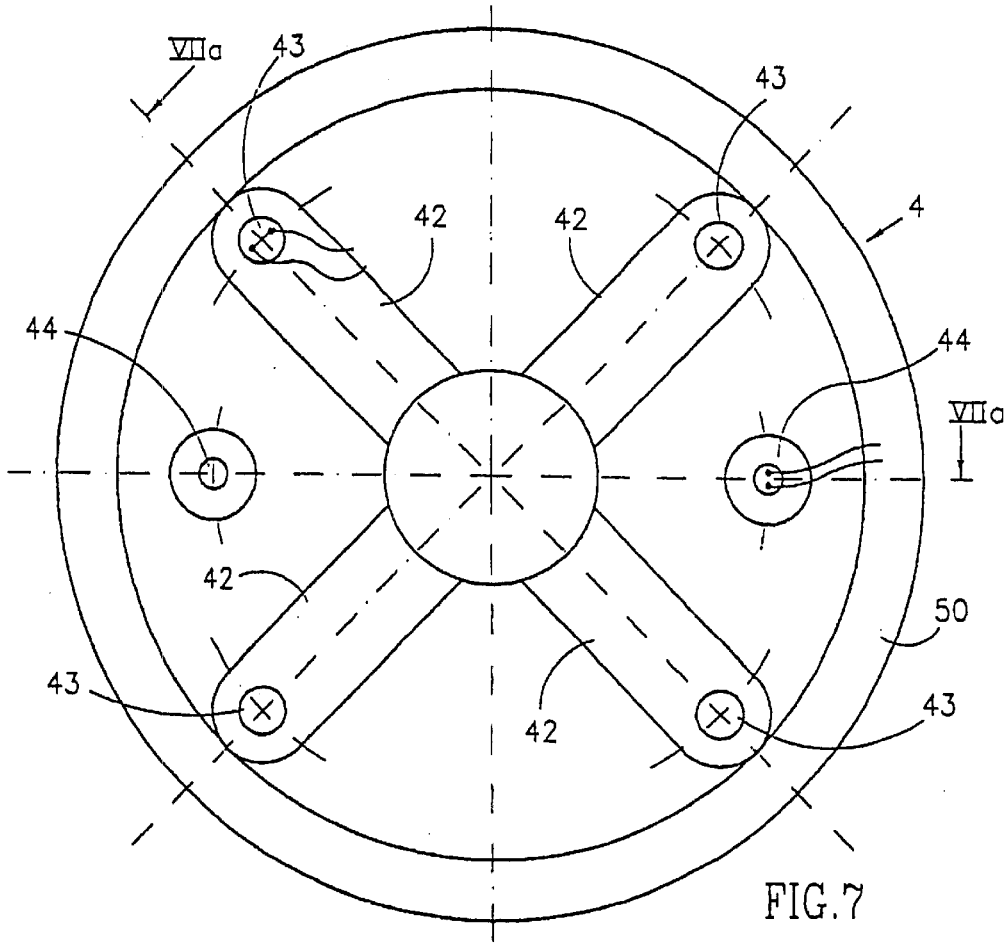
FIG.7
FIG.7A
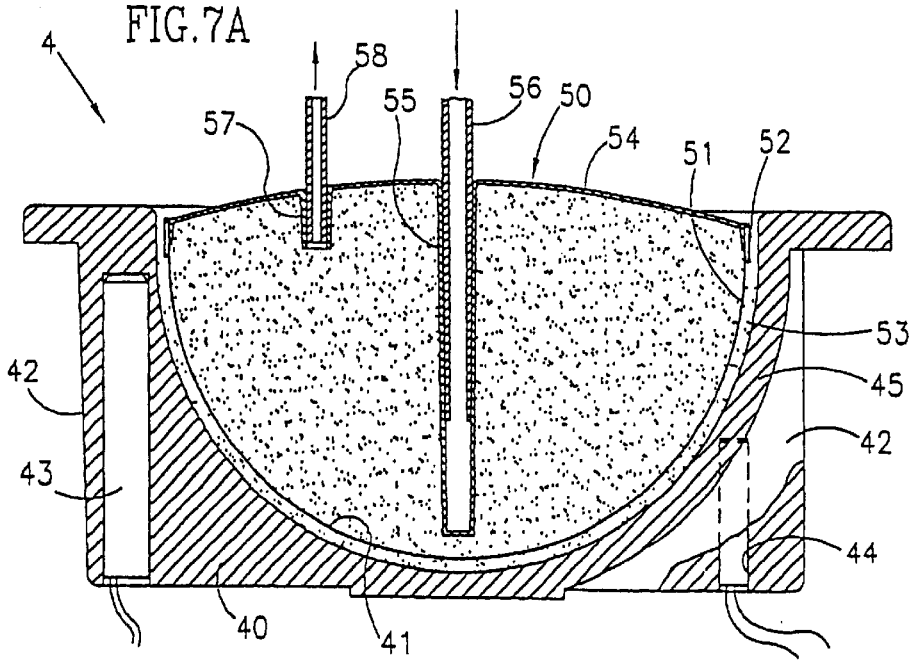

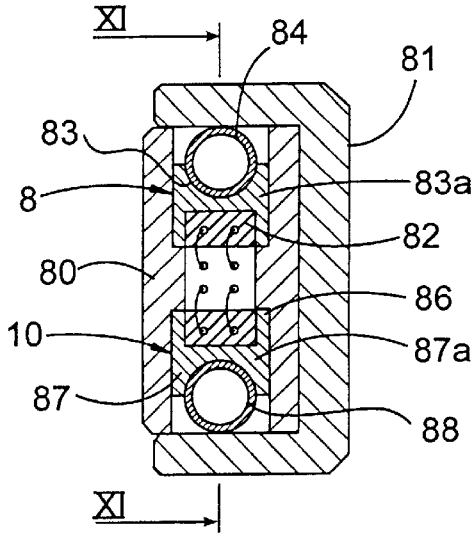
FIG.10
AMENDED

THERMAL TREATMENT APPARATUS

Matter enclosed in heavy brackets [ ] appears in the original patent but forms no part of this reissue specification; matter printed in italics indicates the additions made by reissue.

[RELATED APPLICATION

This application is for a continuation-in-part of my prior patent application Ser. No. 07/669,366, filed Mar. 14, 1991 now U.S. Pat. No. 5,257,977.]

FIELD AND BACKGROUND OF THE INVENTION

The present invention relates to thermal treatment apparatus for thermally treating selected tissues of a subject. The invention is particularly useful as a thermal treatment apparatus for treating prostate, bladder and uterus, and is described below particularly with respect to an apparatus for treating the prostate. The invention also relates to a catheter construction, a heater, a peristaltic pump, and a thermal sensor assembly, all especially useful in the novel thermal treatment apparatus.

Thermal treatment is now a recognized form of treatment of certain types of ailments including benign prostatic hyperplasia (BPH), prostatitis, and prostate cancer. My prior U.S. application Ser. No. 07/669,366, filed Mar. 14, 1991, now U.S. Pat. No. 5,257,977 discloses one form of thermal treatment apparatus including a catheter insertable into the subject's urethra. The proximal end of the catheter includes an inflatable anchoring section in the form of a balloon to be anchored in the subjects bladder, and a heating section which, when the balloon is so anchored, extends through the subject's prostate. A heated liquid, such as water, is used to inflate the balloon and is also circulated through the heating section to heat the adjacent tissues of the prostate and the bladder neck.

The present invention relates to this type of thermal treatment apparatus but provides a number of important advantages, as will be described more particularly below.

BRIEF SUMMARY OF THE INVENTION

According to the present invention, there is provided a thermal treatment apparatus for thermally treating selected tissues of a subject located in or near a body cavity, comprising a catheter insertable into the subject's body cavity and including a proximal end formed with an inflatable anchoring section for anchoring the catheter in the body cavity, a distal end to be located externally of the body cavity, and an inflatable heating section adjacent the proximal end to be located near the tissue to be heated. The catheter is formed with first and second passageways extending from the distal end to the, inflatable heating section for circulating heated fluid through the inflatable heating section but not through the inflatable anchoring section; and a third passageway from the distal end to the inflatable anchoring section for inflating the inflatable anchoring section with a non-heated fluid, whereby the inflatable heating section and the tissue in its proximity may be heated to a desired high temperature without correspondingly heating the inflatable anchoring section and the tissue in its proximity.

By thus inflating the anchoring section at the proximal end of the catheter with a separate, non-heated fluid, the heating fluid may be more particularly targeted, by the inflatable heating section, to the tissue to be subjected to the thermal treatment, thereby enabling higher temperatures to be applied if desired.

According to a another aspect of the invention, there is provided a thermal treatment apparatus for thermally treating selected tissues of a subject located in or near a body cavity, comprising: a catheter insertable into the subject's body cavity and including a proximal end having an inflatable anchoring section for anchoring the catheter in the body cavity, a distal end to be located externally of the body cavity, and an inflatable heating section adjacent the proximal end to be located near the tissue to be heated; first and second passageways from the distal end to the inflatable heating section for circulating heated fluid through the inflatable heating section but not through the inflatable anchoring section; a first thermal sensor assembly near the inlet end of the first passageway for measuring the temperature of the heated fluid entering the first passageway; and a second thermal sensor assembly near the outlet end of the second passageway for measuring the temperature of the heated liquid exiting from the second passageway.

More particularly, each of the two thermal sensor assemblies includes: a thermal sensor, a metal tube connectable to the respective end of the respective passageway of the catheter to receive the heated fluid flowing therethrough; a metal thermal coupling member formed with a recess on one face for receiving the thermal sensor therein, a recess on the opposite face complementary to the shape of the metal tube for receiving the metal tube therein, and a relatively thin web between the two recesses; and a cover pressing the metal tube to the metal thermal coupling member.

According to a still further aspect of the invention, there is provided a liquid heater which is particularly useful in such thermal treatment apparatus and including a heating block formed with a semi-spherical cavity; a container defining a liquid reservoir and also formed with a semi-spherical wall removably receivable in the cavity of the heating block; a cover attached to the container; a liquid inlet tube passing through the cover for inletting a liquid into the container to be heated by the heating block; and a liquid outlet tube passing through the cover for outletting a liquid from the container after having been heated by the heating block.

According to a further aspect of the invention, there is provided a peristaltic pump particularly useful in thermal treatment apparatus, which peristaltic pump includes a housing formed with a cylindrical cavity; and a rotor rotatably mounted within the cavity and carrying rollers engageable with a peristaltic tube insertable into the cavity for pressing the peristaltic tube against a wall of the housing in order to pump a liquid through the peristaltic tube during the rotation of the rotor; the wall of the housing including a skirt depending from a lid removably received over the cylindrical cavity; the depending skirt extending less than the circumference of the lid to produce an interruption in the housing wall against which the peristaltic tube is pressed by the rollers of the rotor.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a block diagram illustrating the main components of a thermal treatment apparatus constructed in accordance with the present invention;

FIGS. 4, 5 and 6 are transverse sectional views along lines IV—IV, V—V and VI—VI in FIG. 3;

FIG. 7 is a bottom view illustrating one form of liquid heater constructed in accordance with the invention for use in the thermal treatment apparatus of FIG. 1;

FIG. 7*a* is a sectional view along line VIIa—VIIa of FIG. 7;

FIG. 10 is a transverse sectional view along line X—X of FIG. 11.

DESCRIPTION OF A PREFERRED EMBODIMENT

Overall Apparatus

Figure 2:
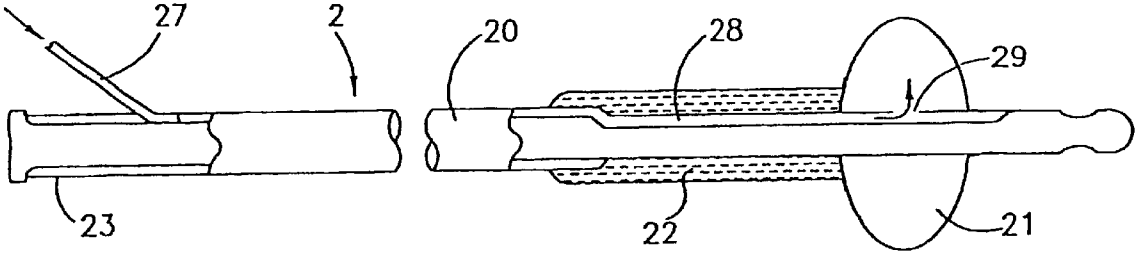
FIG. 2 is a view, partially in longitudinal section diagrammatically illustrating one form of catheter constructed in accordance with the present invention for use in the thermal treatment apparatus of FIG. 1.
Figure 3:
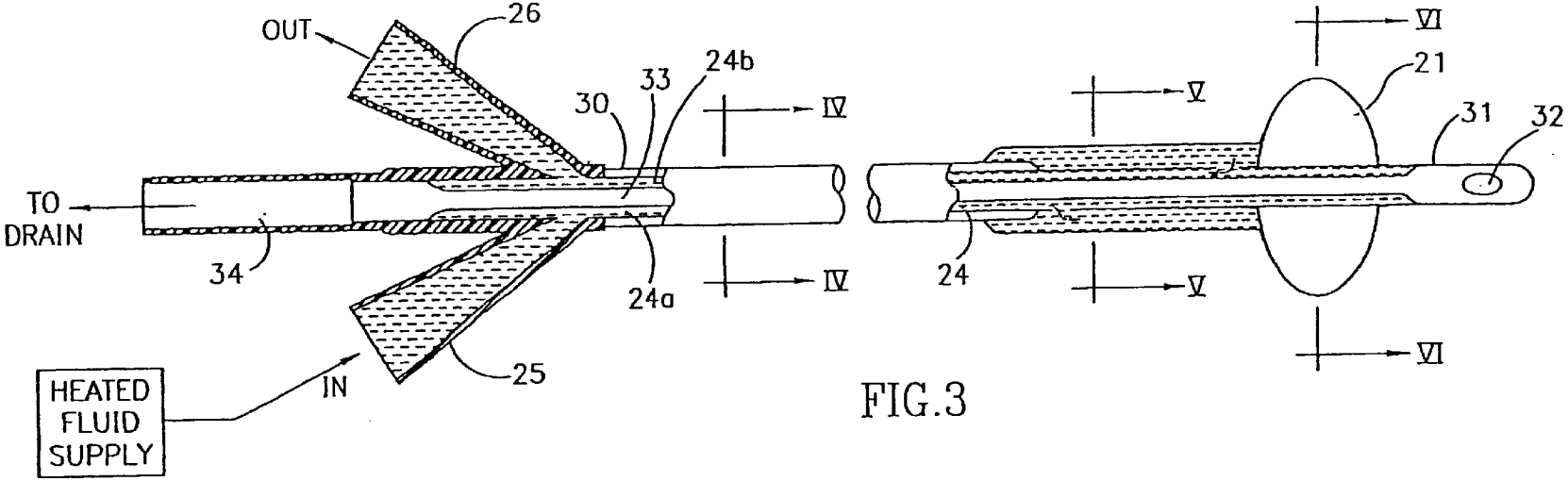
FIG. 3 is a view, partially in longitudinal section and rotated 90° with respect to FIG. 2, illustrating the catheter of FIG. 2.

The thermal treatment apparatus diagrammatically illustrated in FIG. I includes a catheter 2 insertable into a subject's body cavity to be treated thermally. In the example to be described below, the heat is applied to treat the prostate. The catheter 2 would therefore be inserted into the subject's urethra, such that one end of the catheter is anchored in the subject's bladder. This locates a heating section of the catheter in the subject's prostate.

The thermal treatment apparatus illustrated in FIG. 1 further includes a heater 4 for heating a fluid, in this case a liquid such as water, to be circulated in a closed circuit through the heating section of the catheter by means of a pump 6, The temperature of the heating liquid inletted from pump 6 into the catheter 2 is measured by a thermal sensor assembly 8, and the temperature of the liquid exiting from the catheter 2 to the heater 4 is measured by another thermal sensor assembly 10. The illustrated apparatus further includes a controller 12 which controls both the heater 4 and the pump 6 in response to the temperature sensed by sensor assemblies 8 and 10 and another sensor (to be described below) in the heater 4.

Figure 8:
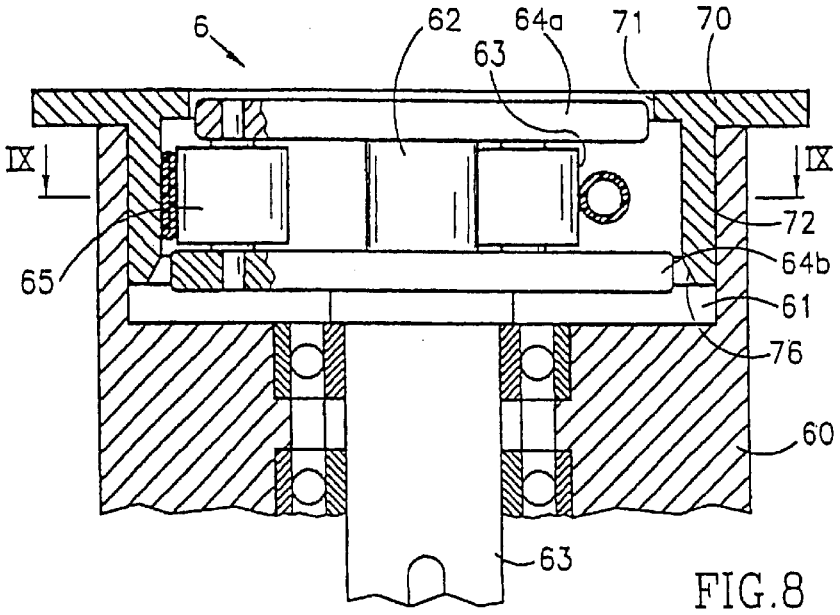
FIG. 8 is a longitudinal sectional view along line VIII—VIII of FIG. 9.
Figure 9:
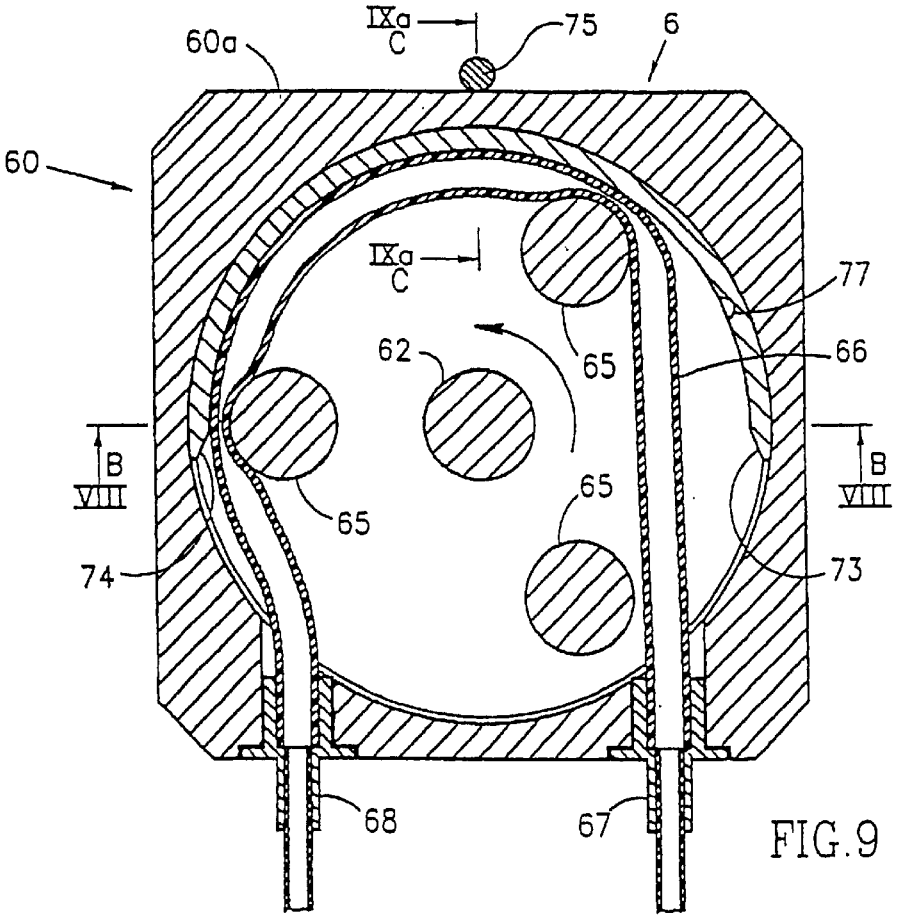
FIG. 9 is a transverse sectional view along line IX—IX of FIG. 8, of one form of peristaltic pump constructed in accordance with the invention, FIG. 9*a* being a fragmentary detail view along line IXa—IXa of FIG. 9.
Figure 9A:
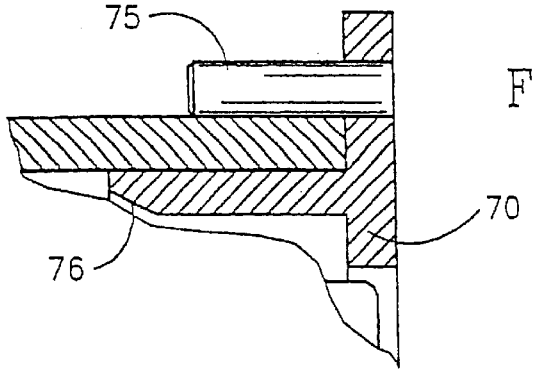
Figure 11:
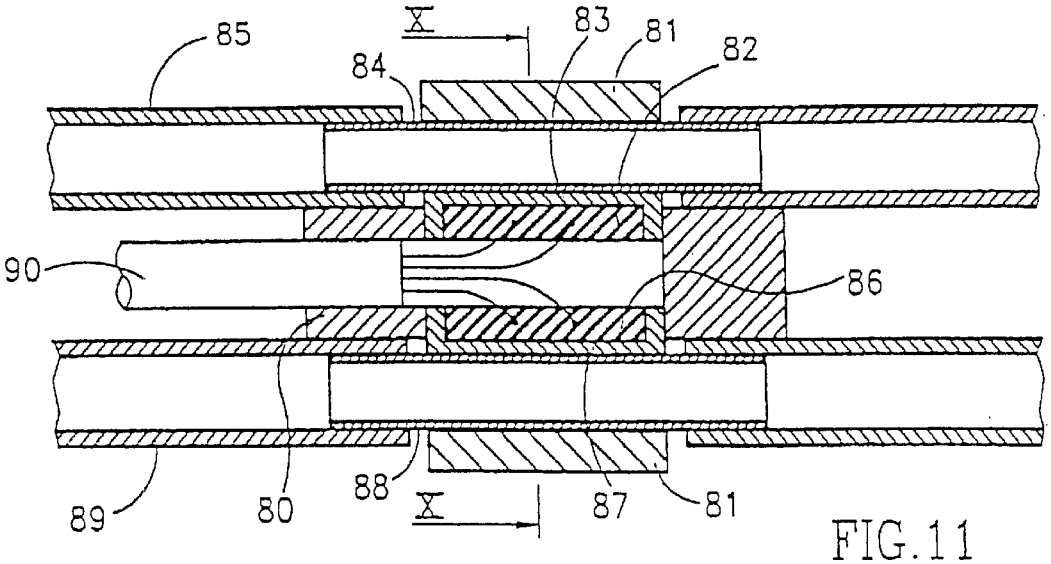
FIG. 11 is a longitudinal sectional view along line XI—XI of FIG. 10, illustrating one form of thermal sensor assembly constructed in accordance with the invention for use in the thermal treatment apparatus of FIG. 1.

The construction of the catheter 2 is shown in FIGS. 2–6; the construction of the liquid heater 4 is shown in FIGS. 7 and 7*a*; the construction of the pump 6 is shown in FIGS. 8, 9 and 9*a*; and the construction of the two thermal sensor assemblies 8 and 10 is shown in FIGS. 10 and 11.

The catheter 2, as shown in FIGS. 2–6, includes a long slender tube 20 formed with an inflatable anchoring section 21 at the proximal end for anchoring the catheter in the subject's bladder, and thereby for locating an inflatable cylindrical heating section 22 extending through the subject's prostate when the catheter is so anchored. The opposite end of the catheter, called the distal end, is to be located externally of the subject's urethra so as to be readily accessible for inflating the proximal anchoring section 21 and for inflating and circulating a heating liquid through the inflatable heating section 22.

The heating liquid is circulated through the inflatable heating section 22 via two passageways 24*a*, 24*b* having an inlet 25 and an outlet 26 at the distal end 23 of the catheter. The inflatable anchoring section 21 of the catheter is inflated by an unheated fluid, such as air, introduced via an inlet 27 at the distal end 23 and communicating with the anchoring section 21 via the third passageway 28 and an opening 29.

The portion of the catheter from the distal end 23 to the inflatable heating section 22 is thermally insulated from the subject's tissue by means of outer chambers 30, 30*a* and 30*b* enclosing passageways 24*a*, 24*b*, referred to generically by numeral 24, through which the heating liquid is circulated to the heating section 22. One of these chambers communicates with passageway 28 through which unheated air is applied to inflate the anchoring section 21.

The catheter also includes an extension 31 at the proximal end, which extension is received within the subject's bladder. Extension 31 is formed with an opening 32 for draining the subject's bladder via a passageway 33 passing through the length of the catheter and terminating in an outlet 34 at the distal end 23 of the catheter for connection to a drain. Extension 31 and its passageway 33 may also be used for introducing a drug into the bladder if desired.

The Heater 4 (FIG. 7)

The liquid heater 4, as more particularly illustrated in FIG. 7, includes a heating block 40 made of a good heat-conducting material, such as aluminum. Heating block 40 is of dome shape to define a smoothly curved semi-spherical cavity 41, and is integrally formed with four perpendicular ribs 42. A plurality of electrical heating elements 43, and one or more thermal sensors 44, are encased within the heating block 40. As seen in FIG. 7, an electrical heating element 43 is encased in each of the four ribs 42, and thermal sensor 44 is encased in each of the two opposite sides of the heating block, midway between two heating elements 43. The dome-shaped section of the heating block is relatively thin, as shown at 45 in FIG. 7*a*, to thereby reduce its thermal mass.

The heating block 40 illustrated in FIG. 7*a* further includes a removable container 50 serving as a water reservoir and formed with a complementary-curved wall 51, i.e., of semi-spherical configuration corresponding to the semi-spherical configuration of cavity 41. The semi-spherical wall 51 of container 50, however, is of slightly smaller dimensions than the heating block cavity 41 so as to provide a small gap 52 adapted to receive a small quantity of a liquid 53 to provide a good thermal coupling between block 40 and container wall 51. The semi-spherical shape of the container wall 51 permits it to be of a thin- wall construction and therefore sufficiently inexpensive so as to be disposable after one-time use. The thinness of the plastic wall also provides good thermal conductivity between heating block 40 and the interior of container 50.

Container 50 further includes a cover 54, preferably bonded by an adhesive or solvent or welded to the curved wall 51 of the container. Cover 54 is formed with a reentry tube 55 substantially centrally of the cover for receiving an inlet tube 56 which inlets into the container the liquid to be heated by the heating block 40. A second reentry tube 57 is formed in cover 54 laterally Of reentry tube 55, for receiving the outlet tube 58 which outlets the liquid from the container. The inlet reentry tube 55 extends from cover 54 substantially to the bottom of the container 50, whereas the outlet reentry tube 57 terminates close to the top of the container 50. This arrangement provides a relatively large residence time and contact surface for heating the liquid as it is circulated within container 50 from the inlet 56 to the outlet 58.

The Peristaltic Pump 6 (FIGS. 8, 9 and 9a)

Pump 6 in FIG. 1 is a peristaltic pump as more particularly illustrated in FIGS. 8, 9 and 9*a*. It includes a housing 60 formed with a cylindrical cavity 61. Disposed within cylindrical cavity 61 is a rotor 62 connected by a drive shaft 63 to a gear motor (not shown) and including a pair of spaced discs 64*a*, 64*b* rotatably mounting between them a plurality (3) of rollers 65 within cavity 61. Also located within the cylindrical cavity 61 is a peristaltic tube 66 which is engageable by the roller 65 for pumping the liquid through the tube during the rotation of rotor 62. Assuming rotor 62 is rotated counter-clockwise in FIG. 9, the liquid will be pumped through the peristaltic tube 66 from an inlet nipple 67 to an outlet nipple 68.

As shown in FIG. 8, housing 60 further includes a lid 70 formed with a large central opening 71 for accommodating disc 64 of the rotor 62. Lid 70 is formed with a depending skirt 72 which extends into the cylindrical cavity 61 such that the peristaltic tube 66 is located between the inner surface of skirt 72 and the rollers 65. Skirt 72 extends only for a part of the circumference of the lid, e.g., from 160° to 200°, to accommodate the inlet and outlet ends of the peristaltic tube 66. As shown in FIG. 9, skirt 72 extends slightly more than 180°; also, its leading edge 73 and its trailing edge 74 are tapered to provide a gradual application of the pressure to the peristaltic tube by the roller 65, and a gradual release of the pressure.

Housing 60 is of polygonal, preferably square, cross-section to provide a flat surface 60*a*. Lid 70 is provided with a depending pin 75 in contact with the outer flat surface 60*a* of housing 60 (see FIGS. 9 and 9*a*) to prevent rotation of the lid during the rotation of the rotor 62.

The illustrated construction, including the depending skirt 72, facilitates the assembly of the peristaltic pump with the peristaltic tube 66 between the skirt and the rollers 65. Thus, with the lid removed the peristaltic tube 66 may be conveniently applied around the rollers 65. The lid 70 may then be applied with its skirt 72 received between the peristaltic tube 66 and the inner surface of the cylindrical cavity 61 formed in housing 60, so as to squeeze the tube between it and the rollers 65. For this purpose, the lower edge of skirt 72 is tapered, as shown at 76 in FIGS. 8 and 9*a*, to facilitate the application of the skirt.

The foregoing construction not only facilitates the assembly of the peristaltic pump, but also covers the rollers 65 to minimize exposure to a person's fingers or the like. In addition, the thickness of skirt 72 influences the outlet pressure produced by the pump, so that lids 70 with different thickness skirts 72 may be provided to provide different outlet pressures. In addition, the inner surface of the skirt 72 may be provided with one or more grooves, as shown at 77 in FIG. 9, to produce a pulsatile output.

The thermal sensors assemblies 8, 10

The thermal sensor assemblies 8, 10 are more particularly illustrated in FIGS. 10 and 11. They are both enclosed within a common housing 80 in the shape of an "H" and closed by a common cover 31. Thermal sensor assembly 8 near the inlet end of the catheter 2 includes a thermal sensor element 82 received within a rectangular recess formed in a metal thermal coupling member 83. The opposite face of the coupling member is formed with a recess for receiving a metal tube 84 connectable to an inlet tube 85 near the inlet end of the catheter. Thermal sensor assembly 10 similarly includes a therm[r]al sensor element 86 received within a recess formed in another thermal coupling member 87. The opposite face of member 87 is similarly formed with a recess for receiving a metal tube 88 adapted to be coupled to an outlet tube 89 near the outlet end of the catheter. Electrical connections are made to the two thermal sensor elements 82 and 86 via a cable 90 leading to the controller 12 in FIG. 1.

The two thermal coupling members 83, 87, as well as the two tubes 84, 88, are of a metal, such as stainless steel, having relatively good thermal conductivity. The coupling members 83, 87 include relatively thin web portions 83*a*, 87*a*, respectively, between the thermal sensor elements 82, 86 and the metal tubes 84, 88, so as to provide a good thermal coupling between the liquid flowing through the two metal tubes and their respective thermal sensor elements. The cover 81, fixed to the common H-shaped housing 80 in any suitable manner, presses the metal tubes 94, 88 firmly against their respective metal coupling members 83, 87.

Overall Operation

The overall operation of the thermal treatment apparatus illustrated in the drawings is as follows:

The catheter 2 is inserted into the urethra of the subject until the inflatable anchoring section 21 at the proximal end passes through the subject's bladder neck. An unheated fluid, preferably air, is introduced via inlet 27 and passageway 28 into the interior of the anchoring section 21 to inflate it. This anchors section 21 in the subject's bladder, whereupon the cylindrical heating section 22 of the catheter extends through the subject's prostate.

A heating fluid, such as water, is then pumped from the container 50 via pump 6 into the inlet 25 of passageway 24*a*, to fill the catheter and to inflate the cylindrical heating section 22 of the catheter. Additional water is added to the catheter (e.g., via a separate inlet in the connector connecting the catheter to the closed circuit) to completely fill the closed circuit including container 50 and the catheter 2. The water heated within container 50 is circulated by the peristaltic pump 6 through the closed circuit including the cylindrical heating section 22 of the catheter.

During the circulation of the heating liquid, the sensor assemblies 8, 10 sense the temperature of the heating liquid near the inlet and outlet ends of the catheter, respectively. These sensor assemblies, together with the thermal sensors 44 in the electrical heater 4, control the controller 12 to maintain the desired temperature. Only the inflated heating section 22 of the catheter is effective to heat tissue, because of the thermal insulation provided by the unheated air within the anchoring section 21 of the catheter, and within chambers 30 of the remaining portion of the catheter. Accordingly, the liquid applied to the inflatable heating section 22 may be heated to a relatively high temperature for application to the tissue within the prostate, with less danger of unduly heating other tissue contacted by the catheter. The inflation of the heating section 22 of the catheter also presses that section firmly against the tissue to be thermally treated thereby further enhancing the heating effects.

Drain opening 32 at the proximal end of the catheter, and passageway 33 through the catheter, provide a drain for the bladder liquids or enable the introduction of a drug into the bladder.

While the invention has been described with respect to one preferred embodiment, it will be appreciated that many other variations, modifications and applications of the invention may be made.

What is claimed is:

1. Thermal treatment apparatus for thermally treating selected tissues of a subject located in or near a body cavity, comprising a catheter insertable into the subject's body cavity and including a proximal end to be inserted into the body cavity, a distal end to be located externally of the body cavity, *an inflatable anchoring balloon positioned adjacent said proximal end,* and an inflatable heating section on said proximal end *axially away from said inflatable anchoring balloon in a direction which is toward said distal end so as* to be located near the tissue to be heated; said catheter being formed with first and second passageways extending from said distal end to said inflatable heating section and in fluid communication with each other for circulating heated fluid through said inflatable heating section *and a third anchoring inflation passageway extending from said distal end to said inflatable anchoring balloon, said anchoring inflation passageway configured separate from said first and second passageways,* and thermal insulation, surrounding said first and second passageways from close to said distal end to close to said inflatable heating section, said thermal insulation including a plurality of separate compartments containing a non-heated fluid, said components extending axially along the catheter, whereby the inflatable heating section and the tissue in its proximity may be heated to a desired high temperature without correspondingly heating non-selected tissues.

2. The apparatus according to claim 1, further including a heater associated with said first passageway for heating a fluid, and a pump associated with said heater and said second passageway for circulating said fluid in a closed circuit through said heating section of the catheter.

3. The apparatus according to claim 2, wherein said heater includes: a heating block formed with a smoothly curved cavity; a container defining a liquid reservoir and formed with a complementary-curved wall removably receivable in said cavity; a cover attached to said container; a liquid inlet tube passing through said cover for inletting a liquid into said container to be heated by said heating block; and a liquid outlet tube passing through said cover for outletting a liquid from said container after having been heated by said heating block.

4. The apparatus according to claim 3, wherein the dimensions of said curved wall of the container are slightly smaller than those of the smoothly curved cavity of the heating block, to provide a small gap for receiving a liquid having good thermal coupling characteristics.

5. The apparatus according to claim 3, wherein said smoothly-curved cavity of the heating block, and said complementary-curved wall of the container, are both of semi-spherical configuration.

6. The apparatus according to claim 3, wherein said heating block is made of a material having high thermal conductivity and includes at least one electrical heating element encased therein.

7. The apparatus according to claim 2, wherein said pump is a peristaltic pump for pumping fluid through a peristaltic tube, said pump including:

(a) a housing formed with a substantially cylindrical cavity having an inner surface, said housing provided with a lid, said lid having a depending skirt removably engagable within said cylindrical cavity so as to form an inset lining around a part of said inner surface; and (b) a rotor rotatably mounted within said cylindrical cavity, said rotor carrying rollers, such that, when said depending skirt is not engaged in said cylindrical cavity, the peristaltic tube may be easily inserted between said rollers and said inner surface and, when said depending skirt is engaged in said cylindrical cavity, the peristaltic tube is engaged between said rollers and said inset lining such that rotation of said rotor pumps fluid through the peristaltic tube.

8. The apparatus according to claim 7, wherein an inner surface of said depending skirt is formed with a groove to produce a pulsatile fluid flow.

9. The apparatus of claim 1, further including a first thermal sensor assembly associated with the inlet end of said first passageway for measuring the temperature of the heated fluid entering said first passageway; and a second thermal sensor assembly associated with the outlet end of said second passageway for measuring the temperature of the heated fluid exiting from said second passageway.

10. The apparatus according to claim 9, wherein each of said thermal sensor assemblies includes: a thermal sensor, a metal tube connectable to the respective end of the respective passageway of the catheter to receive the heated fluid flowing therethrough; a metal thermal coupling member formed with a recess on one face for receiving the thermal sensor therein, a recess on the opposite face complementary to the shape of the metal tube for receiving the metal tube therein, and a relatively thin web between the two recesses; and a cover pressing said metal tube to said thermal coupling member.

11. The apparatus according to claim 1, wherein said catheter includes a [third] *fourth* passageway extending centrally of the catheter and communicating with an opening in the proximal end of the catheter to drain liquid from the body cavity to said distal end or to introduce a drug into the body.

12. The apparatus according to claim 1, wherein said heating section of the catheter is of cylindrical configuration.

13. Thermal treatment apparatus for thermally treating selected tissues of a subject located in or near a body cavity, comprising: a catheter insertable into the subject's body cavity and including a proximal end *with a length which is* to be inserted into the body cavity, a distal end to be located externally of the body cavity, and an inflatable heating section [on] *located along a portion of the length of* said proximal end to be located near the tissue to be heated *such that it can be inserted and positioned in a desired location within a body cavity*; first and second passageways *extending* from said distal end to said inflatable heating section in fluid communication with each other [are] for circulating heated fluid through said inflatable heating section; a first thermal sensor assembly associated with the inlet end of said first passageway for measuring the temperature of the heated fluid entering said first passageway; a second thermal sensor assembly associated with the outlet end of said second passageway for measuring the temperature of the heated fluid exiting from said second passageway; and thermal insulation surrounding said first and second passageways from close to said distal end to close to said inflatable heating section, said thermal insulation including a plurality of separate compartments containing a non-heated fluid, said compartments extending axially along [the] *said* catheter.

14. The apparatus according to claim 13, wherein each of said thermal sensor assembly includes: a thermal sensor; a metal tube connectable to the respective end of the respective passageway of the catheter to receive the heated fluid flowing therethrough; a metal thermal coupling member formed with a recess on one face for receiving the thermal sensor therein, a recess on the opposite face complementary to the shape of the metal tube for receiving the metal tube therein, and a relatively thin web between the two recesses; and a cover pressing said metal tube to said metal thermal coupling member.

*15. The apparatus of claim 1, wherein said body cavity is the urethra and the tissue proximity to said inflatable heating section is the prostate, and wherein, in position, said anchoring balloon resides in the bladder of the subject proximate to the bladder neck.*

*16. The apparatus of claim 15, wherein responsive to inflation of said heating section, said catheter inflatable heating section is configured to expand and press against the*

*prostate to enhance the heating effects provided by exposing the tissue to heated fluid circulating therein.*

*17. The apparatus of claim 2, wherein said pump is configured to provide a pulsatile flow output.*

*18. The apparatus of claim 9, wherein said first and second thermal sensor assemblies each include a metal tube portion configured to allow the heated fluid to flow therethrough and which thermally heat up in response to the heated fluid traveling therethrough.*

*19. The apparatus of claim 11, wherein said anchoring balloon is inflated with air, and wherein the heated fluid circulating through said inflatable heating section comprises water.*

*20. The thermal treatment apparatus of claim 13, wherein each of said first and second thermal sensor assemblies includes:*

*a thermal sensor*

*a metal tube in fluid communication with a respective one of the inlet to said first passageway or the outlet to said second passageway to allow the heated fluid to flow therethrough;*

*a metal thermal coupling member operably associated with said thermal sensor and said metal tube which thermally couples said metal tube and thermal sensor, wherein said metal thermal coupling member is formed with a recess cavity configured to receive at least a portion of said metal tube and hold same firmly therein such that said metal tube abuts said recess cavity.*

*21. The thermal treatment apparatus of claim 20, said catheter further comprising an anchoring balloon positioned on said catheter intermediate said inflatable heating section and said proximal end, and wherein said anchoring balloon is in fluid communication with a third passageway which is in fluid isolation from said first and second passageways.*

*22. The apparatus of claim 21, wherein said body cavity comprises the urethra, wherein the tissue in proximity to said inflatable heating section is the prostate, and wherein, in position, said anchoring balloon resides in the bladder of the subject proximate to the bladder neck.*

*23. The apparatus of claim 22, wherein, responsive to inflation of said inflatable heating section, said catheter inflatable heating section is configured to expand and press against the prostate to enhance the heating effects provided by exposing the tissue to heated fluid circulating therein.*

*24. The apparatus of claim 23, wherein said catheter further comprises a urinary drain port on said proximal end, said urinary drain port including a drain channel which extends from said proximal end to said distal end to allow urine to drain therethrough.*

*25. The apparatus of claim 24, wherein said thermal treatment apparatus further comprises a pump in fluid communication with said first and second passageways that circulates the heated fluid therethrough, and wherein said pump is configured to provide a pulsatile flow output.*

*26. The apparatus of claim 24, wherein said anchoring balloon is inflated with air, and wherein the heated fluid circulating through said inflatable heating section comprises water.*

*27. A thermal treatment system for thermally treating benign prostatic hyperplasia, comprising:*

*a catheter configured to be inserted into the urethra of a subject, said catheter having a length extending from a distal end to a proximate end, said distal end located external of said subject during use and said proximate end configured to reside in the bladder of the subject during use, said catheter comprising;*

*an inflatable anchoring balloon configured to inflate and reside against the bladder neck of the subject to hold said catheter in position,*

*an inflatable heating section configured and sized to be positioned adjacent prostate tissue to be heated during use, said anchoring balloon and said inflatable heating section being arranged on said catheter such that when said anchoring balloon is in position and inflated to reside against the bladder neck, said inflatable heating section is inflated to an expanded configuration such that it firmly presses against the prostate tissue to enhance the heating effects provided by contact with said inflatable heating section;*

*an extension having a bladder drainage port positioned on said proximate end of said catheter, said extension bladder drainage port in fluid communication with a drainage passage extending along the length of the catheter for allowing the bladder to drain urine therethrough;*

*a first inlet passageway and a second outlet passageway extending from said distal end of said catheter to said inflatable heating section configured to circulate heated fluid therethrough;*

*a third passageway extending from said distal end of said catheter to said inflatable anchoring section to direct an inflating fluid thereto, said third passageway being separate from said first and second passageways;*

*thermal insulation surrounding said first and second passageways from close to said distal end to close to said inflatable heating section, said thermal insulation comprising a plurality of separate compartments containing a non-heated fluid, said compartments extending axially along said catheter intermediate said distal end and said inflatable heating section;*

*a liquid reservoir in fluid communication with said catheter;*

*a heater operably associated with said liquid reservoir;*

*a pump operably associated with said liquid reservoir and said catheter for circulating heated fluid through said catheter;*

*a first thermal sensor operably associated with heated fluid traveling into said first inlet passageway;*

*a second thermal sensor operably associated with heated fluid traveling out of said second outlet passageway; and*

*a controller operably associated with said pump, said first thermal sensor, said second thermal sensor, and said heater, wherein said controller controls the operation of said heater and said pump in response to temperatures associated with said heated circulating fluid as sensed by said first and second thermal sensors,*

*wherein said thermal treatment system and said catheter are configured to direct the circulating heated fluid to said prostate to treat benign prostate hyperplasia by exposing tissue in the prostate of the subject to a desired high temperature without correspondingly heating non-selected tissues.*

*28. A thermal treatment system according to claim 27, further comprising first and second metal cylinder segments configured to allow the heated fluid to flow therethrough, said first metal cylinder in fluid communication with said first inlet passageway and said second metal cylinder in fluid communication with said second outlet passageway.*

*29. A thermal treatment system according to claim 27, wherein said inflatable heating section is configured as a cylindrical heating section to radially expand from a first collapsed position to a cylindrically shaped heating configuration having a first radial width during use.*

*30. A thermal treatment system according to claim 29, wherein said inflatable anchoring balloon expands to a shape which has a second radial width when inflated, said second radial width being larger than said first radial width of said cylindrically shaped heating section.*

*31. A thermal treatment system according to claim 30, wherein said catheter is configured to circulate heated water to thermally treat the prostate by exposing same to heated water circulating in said inflatable heating section without correspondingly heating non-selected tissues.*

*32. A thermal treatment system according to claim 31, wherein said inflatable anchoring balloon is inflated by introduction of air therein from said third passageway.*

* * * * *